US008907376B2

(12) United States Patent (10) Patent No.: US 8,907,376 B2
Mascaro et al. (45) Date of Patent: Dec. 9, 2014

(54) STRETCHABLE ELECTRONIC CIRCUIT (71) Applicant: University of Utah Research Foundation, Salt Lake City, UT (US)

(72) Inventors: Stephen Mascaro, Salt Lake City, UT (US); Debra Mascaro, Salt Lake City, UT (US); Jumana Abu-Khalaf, Salt Lake City, UT (US); Jungwoo Park, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/672,362

(22) Filed: Nov. 8, 2012

(65) Prior Publication Data

US 2014/0012106 A1 Jan. 9, 2014

Related U.S. Application Data (62) Division of application No. 12/728,814, filed on Mar. 22, 2010, now Pat. No. 8,329,493.

(60) Provisional application No. 61/210,588, filed on Mar. 20, 2009.

(51) Int. Cl.
| | |
|---|---|
| H01L 29/73 | (2006.01) |
| H01L 29/768 | (2006.01) |
| H05K 1/02 | (2006.01) |
| B29C 45/14 | (2006.01) |
| H05K 3/14 | (2006.01) |
| H05K 3/34 | (2006.01) |
| A61B 5/026 | (2006.01) |
| A61B 5/1455 | (2006.01) |
| H05K 1/18 | (2006.01) |
| H05K 3/28 | (2006.01) |
| A61B 5/0295 | (2006.01) |

(52) U.S. Cl.
CPC ........ *H05K 1/0283* (2013.01); *B29C 45/14639* (2013.01); *H05K 3/143* (2013.01); *H05K 3/3463* (2013.01); *A61B 5/0261* (2013.01); *A61B 5/14552* (2013.01); *H05K 1/183* (2013.01); *H05K 3/284* (2013.01); *H05K 2201/0133* (2013.01); *H05K 2201/10106* (2013.01); *H05K 2201/10121* (2013.01); *H05K 2201/10151* (2013.01); *H05K 2201/1034* (2013.01); *H05K 2201/2072* (2013.01); *H05K 2203/0271* (2013.01); *H05K 2203/128* (2013.01); *H05K 2203/1327* (2013.01); *A61B 5/0295* (2013.01)
USPC ........... 257/181; 257/689; 257/226; 257/424; 257/427; 257/470; 257/E23.065; 257/E23.177

(58) Field of Classification Search
USPC ......... 257/177, 181, 688, 689, 226, 424, 427, 257/470, E23.065, E23.177
See application file for complete search history.

(56) References Cited

U.S. PATENT DOCUMENTS 4,825,879 A * 5/1989 Tan et al. ...................... 600/344
4,830,014 A 5/1989 Goodman et al.
(Continued)

OTHER PUBLICATIONS

Abu-Khalaf et al; Stretchable Fingernail Sensors for Measurement of Fingertip Force; 3rd Joint Eurohaptic Conf. & Symposium; Mar. 18-20, 2009;pp. 625-626.

(Continued)

*Primary Examiner* — Thanh V Pham
(74) *Attorney, Agent, or Firm* — Thorpe North & Western LLP (57) ABSTRACT

A stretchable electronic circuit that includes a stretchable base substrate having a plurality of stretchable conductors formed onto a surface thereof, with both the stretchable base substrate and conductors being bendable together about two orthogonal axes. The stretchable circuit also includes a stretchable sensor layer attached to the base substrate with a cavity formed therein which has a contact point exposing one of the plurality of stretchable conductors. The stretchable electronic circuit further includes a surface mount device (SMD) package with a conductor contact protrusion installed into the cavity, and wherein a substantially constant electrical connection is established between the conductor contact protrusion and the stretchable conductor at the contact point by tensile forces interacting between the stretchable base substrate and the stretchable sensor layer.

13 Claims, 7 Drawing Sheets

(56) References Cited

U.S. PATENT DOCUMENTS

| | | | |
|---|---|---|---|
| 5,224,478 A | | 7/1993 | Sakai et al. |
| 5,237,994 A | * | 8/1993 | Goldberger ............... 600/323 |
| 5,678,544 A | * | 10/1997 | DeLonzor et al. ......... 600/344 |
| 5,776,059 A | | 7/1998 | Kaestle et al. |
| 5,792,052 A | | 8/1998 | Isaacson et al. |
| 6,236,037 B1 | | 5/2001 | Asada et al. |
| 6,388,247 B2 | | 5/2002 | Asada et al. |
| 8,190,224 B2 | | 5/2012 | Hoarau |
| 8,329,493 B2 | | 12/2012 | Mascaro |
| 2005/0286901 A1 | | 12/2005 | Sasser et al. |
| 2008/0091121 A1 | | 4/2008 | Sun et al. |
| 2009/0168374 A1 | | 7/2009 | Clayton et al. |

OTHER PUBLICATIONS

Abu-Khalaf et al; Stretchable Fingernail Sensors for Measurement of Fingertip Force Poster; $3_{rd}$ Joint Eurohaptics Conf. & Symposium; Mar. 18-20, 2009; 1 page.

Brosteaux et al; Design and Fabrication of Elastic Interconnections for Stretchable Electronic Circuits; IEEE Electron Device Letters; Jul. 2007; pp. 552-554; vol. 28, No. 7.

Cho et al; Review of Manufacturing Processes for Soft Biomimetic Robots; KSPE and Springer; Jun. 2009; pp. 171-181.

Engel et al; Multi Layer Embedment of Conductive and Non-Conductive PDMS for All-Elastomer Memes, Micro Actuators, Sensors, and Systems Group; Proc. IEEE MEMS, 2006, pp. 246-250.

Gray et al; High Conductivity Elastomeric Electronics; Advanced Materials; Wiley-VCH Verlag GmbH & Co. KCaA, Weinheim; Mar. 5, 2004; pp. 393-397; No. 5.

Hu et al; Super Flexible Sensor Skin Using Liquid Metal as Interconnect; IEEE Sensors; 2007 Conference; pp. 815-817.

Kim et al; A Biaxially Stretchable Interconnect with Liquid Alloy Joints on Flexible Substrate, Transducers & Eurosensors; 2007; pp. 159-1600.

Kim et al; A Multaxial Strechable Interconnect Using Liquid-Alloy-Filled Elastomeric Microchannels, Applied Physics Letters; 2008; pp. 011904-1-011904-3; vol. 92.

Lacour et al; Design and Performance of Thin Metal Film Interconnects for Skin-Like Electronic Circuits; IEEE Electron Device Letters; Apr. 4, 2004; pp. 179-181; vol. 25, No. 4.

Lacour et al; Stretchable Gold Conductors on Elastomeric Substrates; Applied Physics Letters; Apr. 14, 2003; pp. 2404-2406; vol. 82, No. 15.

Li et al; Stretchabillity of Thin Metal Films on Elastomeric Substrates; Applied Physics Letters; Oct. 18, 2004; pp. 3435-3437; vol. 85, No. 16.

Mascaro et al; Measurement of Finger Posture and Three-Zxis Fingertip Touch Force Using Fingernail Sensors; IEEE Trans. on Robotics and Automation; Feb. 2004; pp. 26-35; vol. 20, No. 1.

Mascaro et al; Photoplethysmograph Fingernail Sensors for Measuring Finger Forces Without Haptic Obstruction; IEEE Trans. on Robotics and Automation; Oct. 2001; pp. 698-708, vol. 17, No. 5.

Mascaro et al; Understanding of Fingernail-Bone Interaction and Fingertip Hemodynamics for Fingernail Sensor Design; Haptic Interfaces for Virtual Environment and Teleoperator Systems; 2002; HAPTICS 2002, $10^{th}$ Symposium on Haptic Interfaces for Virtual Environment and Teleoperator Systems; pp. 106-113.

McAlpine et al; Energy-Harvesting Films could Power Medical Devices; CEP; Mar. 2010; www.aiche.org/cep ; pp. 6-8.

Sun et al; Measuring Fingertip Forces by Imaging the Fingernail; Haptic Interfaces for Virtual Environment and Teleoperator Systems; 2006; pp. 125-131.

Sun et al; Predicting Fingertip Forces by Imaging Coloration Changes in the Fingernail and Surrounding Skin; Nov. 3, 2005; pp. 1-17.

Xiao et al; Stretchable and Compressible Tin Films of Stiff Materials on Compliant Wavy Substrates; Applied Physics Letters; 2008; pp. 013109-1-013109-3; vol. 93.

\* cited by examiner

FIG. 1

SECTION A-A
FIG. 2

STRETCHABLE ELECTRONIC CIRCUIT

RELATED APPLICATION

This application is a divisional application of U.S. application Ser. No. 12/728,814, filed Mar. 22, 2010, entitled "Stretchable Circuit Configuration," which claims the benefit of U.S. Provisional Application No. 61/210,588, filed Mar. 20, 2009, entitled "Stretchable Fingernail Sensors for Measurement of Fingertip Force," which are each incorporated by reference herein.

FIELD OF THE INVENTION

The field of the invention relates generally to electronic circuits, and more specifically to flexible electronic circuits and their methods of manufacture.

BACKGROUND OF THE INVENTION

The application of electronic circuits and devices within and around biological systems, such as living human beings, continues to experience rapid development. Applications for bio-compatible electronics are many, including embedded medical monitoring, diagnostic, treatment and programmable drug dosing devices, for instance, as well as tracking, communication, motion monitoring and motion control devices, etc. In addition to the identification and selection of bio-compatible materials which can withstand intimate contact with living tissue for extended periods of time, a need also exists for electronic circuit configurations that can better conform to the curved, flexible and often moving or flexing surfaces of the living subjects to which the electronic circuits and devices are to be attached.

SUMMARY

A stretchable electronic circuit is provided that includes a stretchable base substrate having a plurality of stretchable conductors formed onto a surface thereof, with both the stretchable base substrate and conductors being bendable together about two orthogonal axes. The stretchable circuit also includes a stretchable sensor layer attached to the base substrate with a cavity formed therein which has a contact point exposing one of the plurality of stretchable conductors. The stretchable electronic circuit further includes a surface mount device (SMD) package with a conductor contact protrusion installed into the cavity, and wherein a substantially constant electrical connection is established between the conductor contact protrusion and the stretchable conductor at the contact point by tensile forces interacting between the stretchable base substrate and the sensor layer.

BRIEF DESCRIPTION OF THE DRAWINGS

Features and advantages of the present invention will be apparent from the detailed description that follows, and when taken in conjunction with the accompanying drawings together illustrate, by way of example, features of the invention. It will be readily appreciated that these drawings merely depict representative embodiments of the present invention and are not to be considered limiting of its scope, and that the components of the invention, as generally described and illustrated in the figures herein, could be arranged and designed in a variety of different configurations. Nonetheless, the present invention will be described and explained with additional specificity and detail through the use of the accompanying drawings, in which.

DETAILED DESCRIPTION OF EXEMPLARY EMBODIMENTS

The following detailed description makes reference to the accompanying drawings, which form a part thereof and in which are shown, by way of illustration, various representative embodiments in which the invention can be practiced. While these embodiments are described in sufficient detail to enable those skilled in the art to practice the invention, it should be understood that other embodiments can be realized and that various changes can be made without departing from the spirit and scope of the present invention. As such, the following detailed description is not intended to limit the scope of the invention as it is claimed, but rather is presented for purposes of illustration, to describe the features and characteristics of the representative embodiments, and to sufficiently enable one skilled in the art to practice the invention. Accordingly, the scope of the present invention is to be defined solely by the appended claims.

Furthermore, the following detailed description and representative embodiments of the invention will best be understood with reference to the accompanying drawings, wherein the elements and features of the embodiments are designated by numerals throughout.

Definitions

In describing and claiming the present invention, the following terminology will be used.

The singular forms "a," "an," and "the" include plural references unless the context clearly dictates otherwise. Thus, for example, reference to "a stretchable conductor" includes reference to one or more of such structures, "a stretchable fill material" includes reference to one or more of such materials, and "a positioning step" refers to one or more of such steps.

As used herein, "longitudinal axis" refers to the long axis or centerline of an elongate or rounded structure.

As used herein, "transverse" refers to a direction that cuts across a referenced plane or axis at an angle ranging from perpendicular to about 45 degrees off the referenced plane or axis.

As used herein, "stretchable electronic circuit" refers to a stretchable base substrate with stretchable conductors formed on or within the base substrate, with both the substrate and conductors being bendable together about at least one axis while maintaining substantially constant electrical connection.

As used herein, "surface mount device (SMD) package" refers to an electronic circuit device which has been made using one or more surface mount technology methods.

As used herein, "substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, and sub-ranges such as 10 to 50, 20 to 100, etc.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Stretchable Electronic Circuits

Illustrated in FIGS. 1-16 are several representative embodiments of a stretchable electronic circuit, which embodiments also include various methods and steps for making the stretchable electronic circuit, such as embedding a surface mount device (SMD) package into a stretchable electronic circuit. As described herein, the stretchable electronic circuit and its methods of manufacture provide several significant advantages and benefits over other flexible electronic devices and construction methods. However, the recited advantages are not meant to be limiting in any way, as one skilled in the art will appreciate that other advantages may also be realized upon applying the stretchable electronic circuit and practicing the various manufacturing methods described herein.

Figure 1:
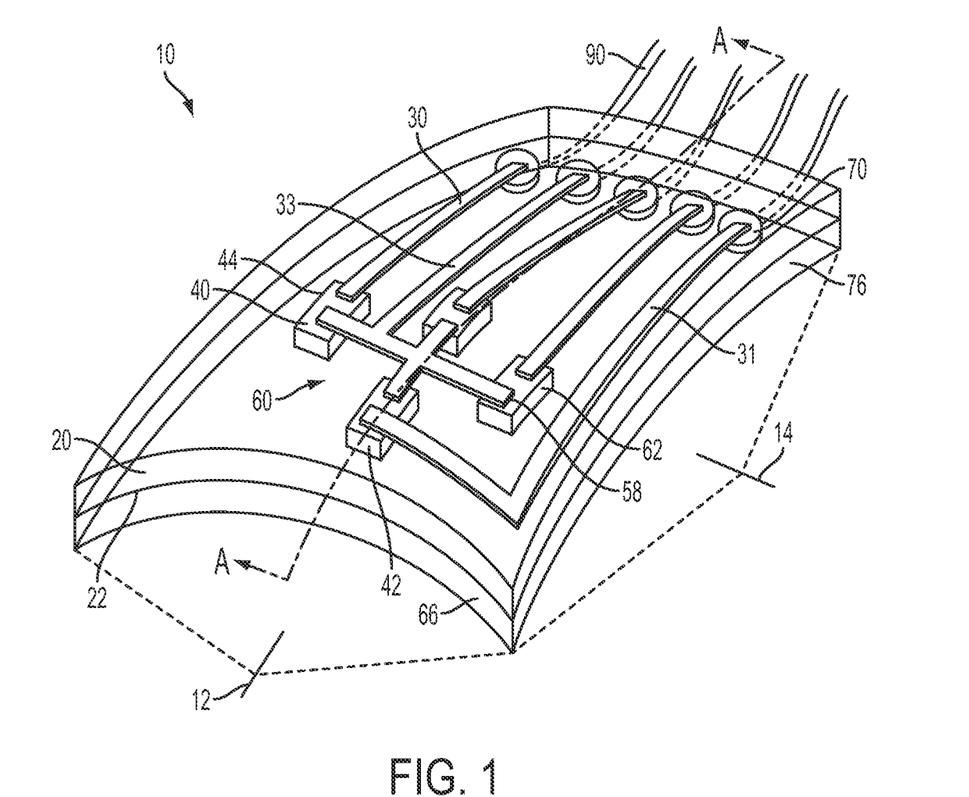
FIG. 1 is a schematic view of a stretchable electronic circuit, in accordance with one embodiment.

FIG. 1 shows an exemplary stretchable electronic circuit 10, in accordance with one representative embodiment. The circuit includes a stretchable base substrate 20 having one or more stretchable conductors 30 formed onto a surface 22 thereof. Both the stretchable base substrate 20 and conductors 30 can be made from selected materials and manufactured in such a way, as discussed below, so as to be simultaneously bendable about at least two axes 12, 14 that are substantially orthogonal to each other. The circuit 10 also includes one or more sensor locations 60 formed into a stretchable sensor layer 66 that is attached or bonded to the stretchable base substrate 20 and which covers, protects and insulates the stretchable conductors 30 except for one or more shaped sensor cavities 62 formed into the sensor layer 66. Each sensor cavity 62 can further include one or more exposed contact points 58 which bare the exposed surfaces of one or more conductors to the interior of the cavity 62.

The stretchable electronic circuit 10 further includes one or more surface mount device (SMD) packages 40 (hereinafter an "SMD package") that are installed into the sensor cavities 62. Each SMD package 40 can have conductor contact protrusions located at the exposed contact points 58, so that a substantially constant electrical connection can be established between the conductor contact protrusions and the stretchable conductors 30 at the contact points 58 by tensile forces interacting between the stretchable base substrate 20 and the stretchable sensor layer 66 which operate to mechanically push the two conductive surfaces together. The conductor contact protrusions can extend either laterally or vertically away from a body of the SMD package, and in one aspect can be substantially flush with a body of the SMD package.

The stretchable electronic circuit 10 can further include one or more liquid flexible contacts 70 which connect an external interface lead wire 90 to one of the stretchable conductors 30. As shown in cross-section in FIG. 2, the liquid flexible contacts 70 can be formed into a stretchable connector layer 76 that is attached or bonded to the stretchable base substrate 20 to cover, protect and insulate the stretchable conductors 30, except for one or more connector wells 72 formed into the connector layer 76 having exposed contact points 88 at the bottoms thereof which bare the conductor to the interior volume of the cavity. One end of an external lead wire 90 can be installed into the connector well 72 before or after filling the well with a liquid metal 78 or similar flowable conductive substance (e.g. conductive polymer) that establishes a substantially constant electrical connection between the lead 90 wire and the stretchable conductor 30. A stretchable cap 92 can then be formed over the cavity to secure the lead wire 90 to the stretchable electronic circuit 10 and seal the liquid metal 78 within the connector well 72.

Each of the stretchable base substrate 20, sensor layer 66, connector layer 76 and the stretchable cap 92 can be formed from one or more flexible, bio-compatible materials such as PDMS (e.g. polydimethylsiloxane) or similar compound that can provide a significant degree of elasticity while withstanding intimate contact with living tissue for extended periods of time. The PDMS compositions can be further advantageous by flowing viscously when heated and being pourable into a mold or similar container for shaping, and which can solidify into an elastic and stretchable rubber-like solid after cooling to room temperature or below the liquidus temperature.

Figure 2:
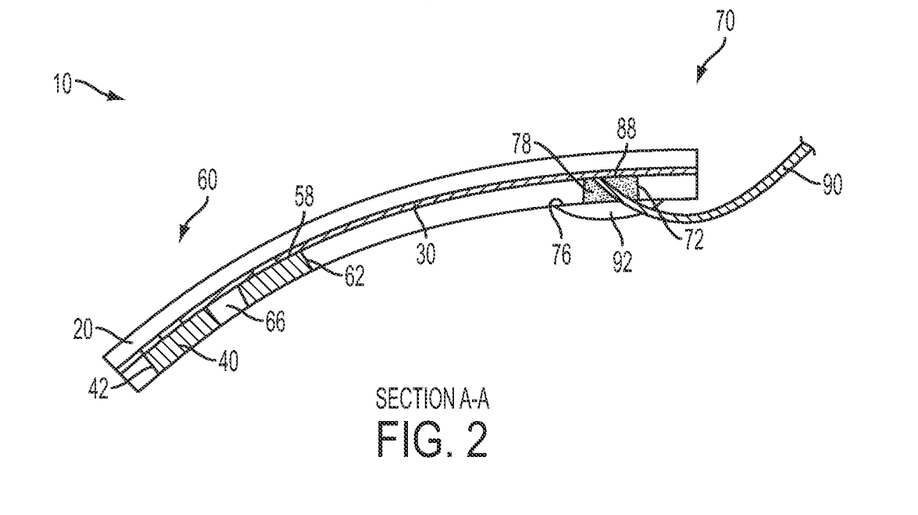
FIG. 2 is a cross-sectional view of the stretchable electronic circuit of FIG. 1 across section A-A.

As can be seen in FIGS. 1 and 2, the stretchable connector layer 76 may or may not be the same as the stretchable sensor layer 66, and may or may not be formed at the same time. Furthermore, the sensor locations 60 can be spaced apart from the liquid flexible contacts 70 and connected to each other by an expanse of stretchable base substrate 20 and conductors 30 which provides the stretchable electronic circuit with a length which can easily bend about the one or more axes 12, 14 and conform to an underlying body member of the living subject, such as a fingernail or patch of skin. In other aspects, however, the sensor locations 60 and liquid flexible contacts 70 can be located adjacent one to another and/or intermixed to minimize the overall size of the stretchable electronic circuit.

The one or more SMD packages 40 installed into the sensor cavities 62 at the sensor locations 60 can further comprise a plurality of different types of SMD packages. For instance, a plurality of light-emitting diodes (LEDs) 42 and photodiode detectors 44 can be arrayed together at the sensor locations 60, with each diode and detector being connected through its own dedicated stretchable signal conductor 31 and liquid flexible contact 70 to a dedicated external interface lead wire 90. As can also be appreciated by one of skill in the art, a stretchable common conductor 33 can also be supplied to the various sensor locations to provide a common ground or neutral connection and complete the electronic circuit.

Figure 3A:
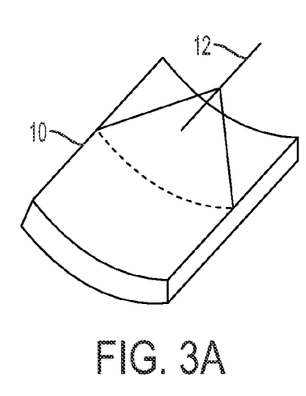
FIGS. 3A-3C are schematic views illustrating the stretchability of the stretchable electronic circuit of FIG. 1 along various axes.
Figures 3B, 3C:
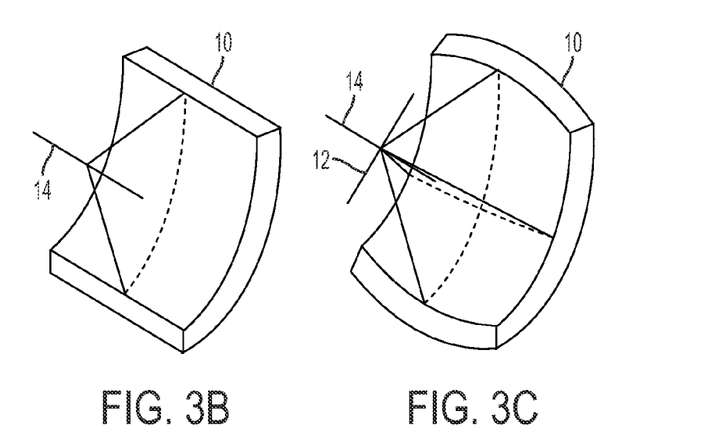

FIGS. 3A-3C together illustrate the stretchability of the stretchable electronic circuit 10 about two axes 12, 14 which can be substantially orthogonal to each other. Although two axes of bending are shown, in one aspect the stretchable electronic circuit 10 may also be bent, stretched or twisted about additional axes or into complex shapes while still maintaining substantially constant electrical connections between the various electrical and/or electronic components embedded or formed into the various layers which form the stretchable circuit 10.

Figure 4A:
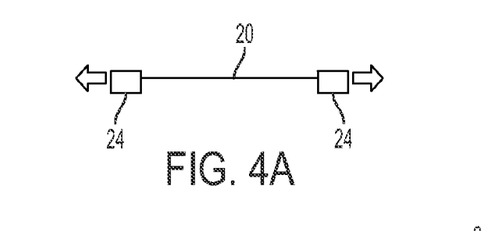
FIGS. 4A-4B together illustrate a stretching jig for stretching the substrate in the manufacture of the stretchable electronic circuit, in accordance with a representative embodiment.
Figure 4B:
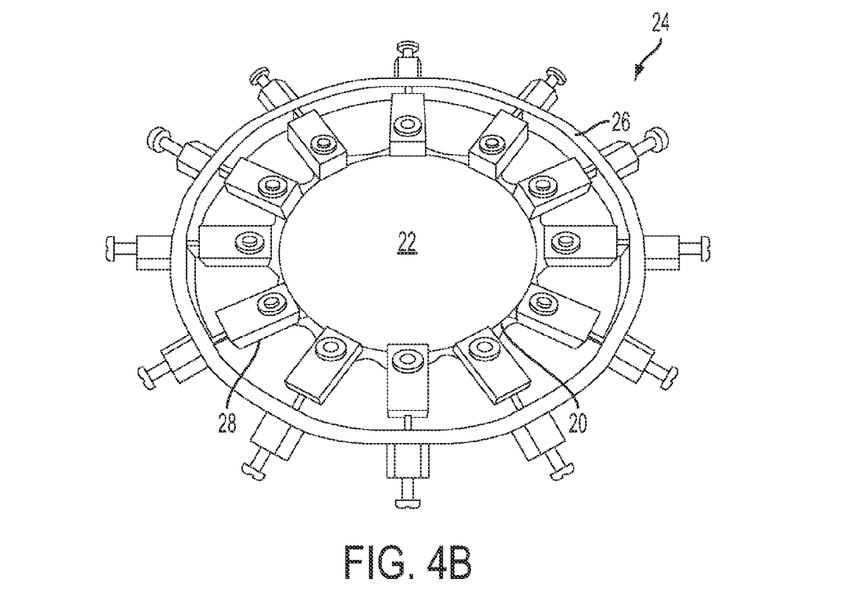
Figure 5:
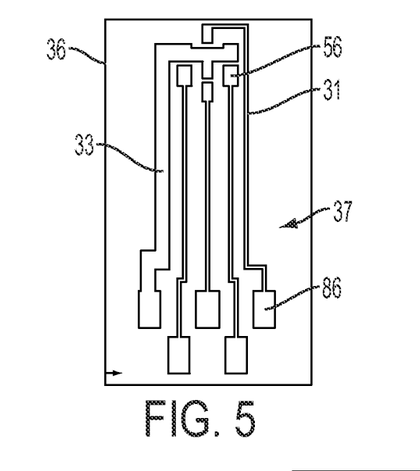
FIG. 5 illustrates an exemplary patterned mask for the evaporative deposition of stretchable conductors on the surface of a stretchable base substrate, in accordance with another representative embodiment.

In accordance with one representative embodiment, FIGS. 4A-4B together illustrate one step in the manufacture of the stretchable electronic circuit which comprises stretching a prepared piece of stretchable material selected for the base substrate 20, such as PDMS, polyurethane, or other elastomeric material, prior to forming the plurality of conductors on the surface 22 thereof. The stretchable material can be stretched in at least two orthogonal or substantially transverse directions, or also radially in a plurality of directions. For instance, the base substrate 20 can be installed into a circular stretching jig 24 having a support ring 26 with a plurality of radially-displaceable clamps 28 equally spaced about the circumference of the ring. As may be appreciated by one of skill in the art, however, both the prepared piece of stretchable material and the stretching jig 24 can have a shape other than circular, such as oval, oblong, square or rectangular. As further shown in FIG. 4B, the base substrate 20 can be installed into the clamps 28, each of which can be displaced outwardly to stretch the base substrate a predetermined strain amount. In one aspect the base substrate can be stretched up to 15% to 54%, or about 40% of its maximum strain. This can result in elongation of up to 50% and in some cases up to 100% or more, depending on the specific design and materials chosen. The specific stretchability can also depend on the nature of the embedded SMD and other components which can sometimes tend to reduce permissible strain.

After stretching the base substrate 20 to the predetermined strain amount, a deposition mask 36 (FIG. 5) having a plurality of patterned openings 37 formed therein, and which correspond in shape to the pattern of stretchable conductors, can be placed over the surface 22 of the base substrate 20. As can be seen, the shapes of the stretchable conductors defined by the patterned openings can include thin stretchable signal conductors 31 corresponding to the signal wires between the installed SMD packages and their output connections, a thick stretchable common conductor 33 corresponding to the neutral or common wire to each SMD package, sensor flats providing the sensor contact points 58 for the SMD packages, and contact flats providing the connector contact points 88 for the liquid flexible contacts.

Figure 6A:
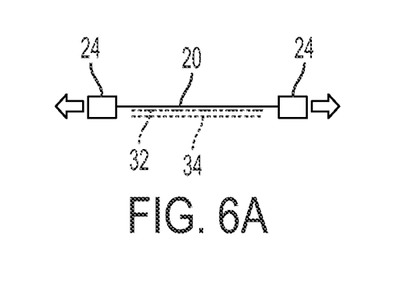
FIGS. 6A-6B together illustrate forming conductive lines during a stretched step in the manufacture of the stretchable electronic circuit, in accordance with a representative embodiment.
Figure 6B:
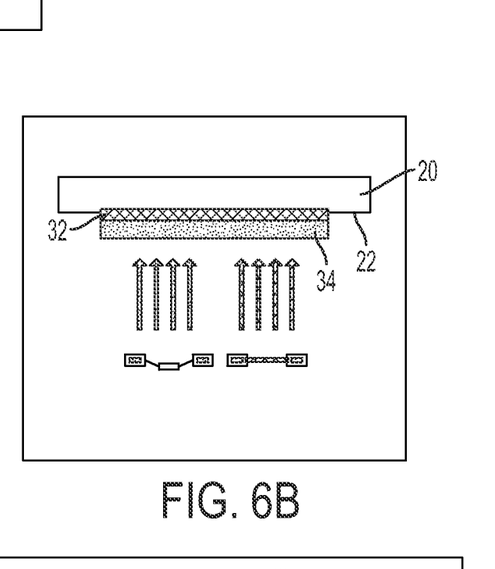

As shown in FIGS. 6A-6B, various layers of conductive materials can then be deposited through the openings in the mask to form the stretchable conductors have the desired material properties. In one aspect, for instance, a first layer 32 of chromium (Cr) of about five nanometers thickness can be deposited onto the surface 22 of the base substrate 20, followed by a second layer 34 of silver (Ag) of about seventy nanometers thickness onto the layer of chromium to complete the stretchable conductors 30. Although the configuration of chromium and silver layers has been identified as being suitable for the stretchable conductors 30 described therein, other conductive metals (e.g. gold, copper, aluminum, and the like), non-metal materials (e.g. conductive polymers), composites thereof, alloys thereof and combinations thereof, and having various thicknesses and configurations, have also been contemplated and are considered to fall within the scope of the present invention.

Figure 7A:
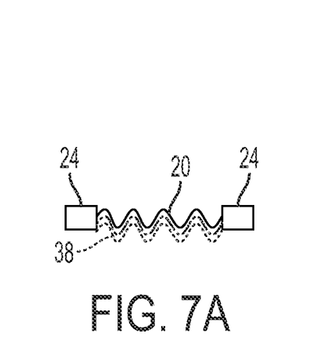
FIGS. 7A-7B together illustrate conductive patterns in a relaxed step in the manufacture of the stretchable electronic circuit, in accordance with a representative embodiment.
Figure 7B:
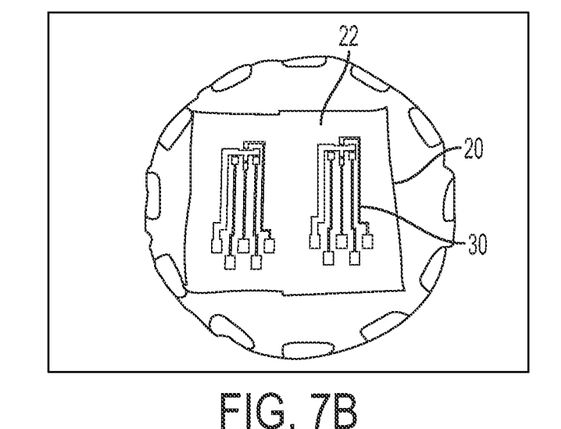

With the formation of the stretchable conductors 30 on the stretched base substrate 20 being complete, the base substrate can be released and removed from the stretching jig, as shown in FIGS. 7A-7B. This can cause the stretchable conductors 30 to buckle or bend into a plurality of folds 38 as the material forming the base substrate 20 springs back into its original non-strained shape and dimensions. Although schematically shown in FIG. 7A as buckling along a single axis, the buckling can actually take place in three dimensions in response to the foundational base substrate 20 being stretched in two or more directions in the stretching jig. As a result, the microstructure of the flexible conductors can take on a crumpled lattice shape that permits stretching about two or more axes, rather than the smoothly-rippled shape shown in FIG. 7A that indicates flexibility along a single axis. From the macroscopic perspective of FIG. 7B, moreover, it can be seen that the overall dimensions and shapes of the un-stretched conductors in FIG. 7B can shrink considerably from the dimensions of the conductor pattern openings 37 formed into the deposition mask 36. (see FIG. 5).

Figure 8A:
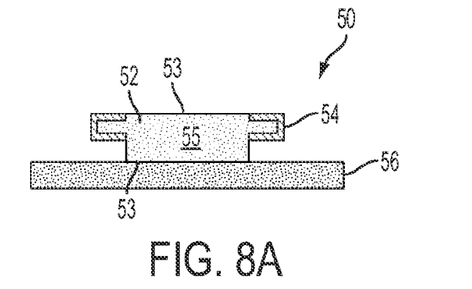
FIGS. 8A-8B together illustrate another step in the manufacture of the stretchable electronic circuit using a rigid plate and first SMD, in accordance with a representative embodiment.
Figure 8B:
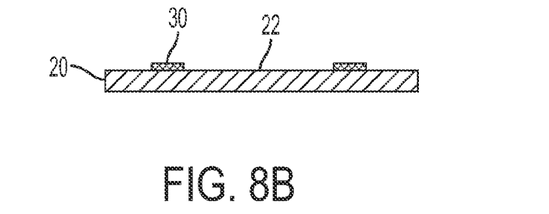

Illustrated in FIGS. 8A-8B and FIGS. 9-12 are several steps in a method for mounting or embedding a surface mount device (SMD) package into the stretchable electronic circuit 10 of FIGS. 1-2. Referring first to FIG. 8A, the method includes forming an SMD mold 50 by mounting the outer face 53 of a first SMD package 52 to a rigid plate 56. The first SMD package may or may not be a functioning SMD package, but can have substantially the same shape and form factor as a second or operational SMD package which will eventually be embedded into the flexible electronic circuit. In one aspect the first SMD package comprises a package body 55 from which extends one or more conductor contact protrusions 54 providing input/output connections for the SMD package, so that the entire SMD package has a generalized "T" shape as shown in FIG. 8A. The method also includes obtaining a base unit 18 for the stretchable electronic circuit, such as the stretchable substrate base 20 having stretchable conductors 30 formed onto a surface 22 thereof, as described above and illustrated in FIG. 8B.

Figure 9:
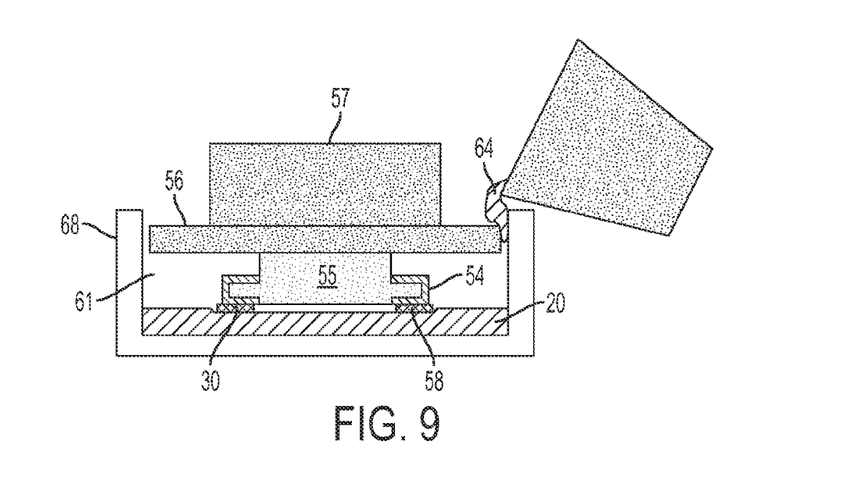
FIG. 9 illustrates pouring a curable material around the first SMD in the manufacture of the stretchable electronic circuit, in accordance with a representative embodiment.
Figure 10:
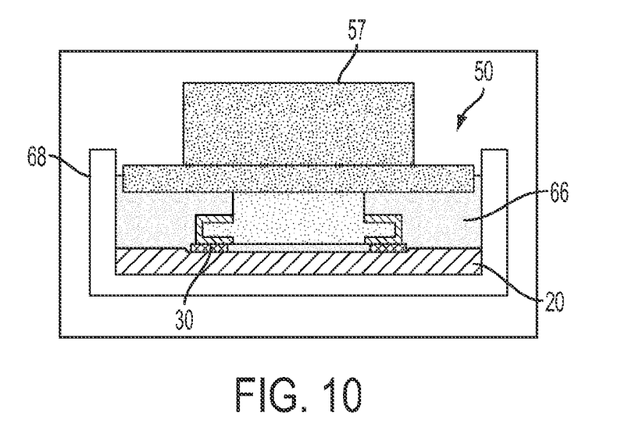
FIG. 10 illustrates an optional preloading of the assembly in the manufacture of the stretchable electronic circuit, in accordance with a representative embodiment.

Referring now to FIG. 9, after the SMD mold 50 has formed it can be inverted and positioned onto the stretchable base substrate 20 which has been pre-positioned within a mold container 68, so that conductor contact protrusions 54 of the first SMD package 52 touch the stretchable conductors 30 on the base substrate 20 and form metal-on-metal (or conductor-on-conductor) contact points 58. Additionally, a weight 57 can also be placed onto the backside the rigid plate 56 to press or compressively preload the SMD mold 50 into the elastic base substrate 20, which can deform slightly under the load. The volume 61 between the base substrate 20 and the rigid plate 56, and which may be bounded on the sides by the mold container 68, can then be filled with uncured stretchable fill material 64 and subsequently be cured or allowed to cure about the SMD mold 59 into a solid stretchable sensor layer 66, as shown in FIG. 10.

The uncured fill material or composition 64 can optionally be thermally heated to a viscously flowing state so that it flows completely around and underneath the body 55 and conductor contact protrusions 54 of the first SMD package 52 shown in FIG. 9. In other aspects, however, the fill material or composition may remain in a viscous or liquid state until cured through exposure to ultraviolet or infrared radiation and the like, or alternatively through one or more chemical processes. In each case, however, the fill material 64 can form a bond with the base substrate 20 as it cures to prevent the base substrate and sensor layer 66 from delaminating over time and use. The resulting cured sensor layer 66 can also be stretchable about two or more axes of bending.

Figure 11:
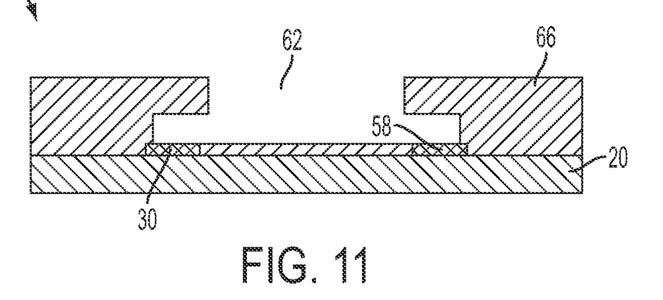
FIG. 11 illustrates the formed empty cavity in the manufacture of the stretchable electronic circuit, in accordance with a representative embodiment.
Figure 12:
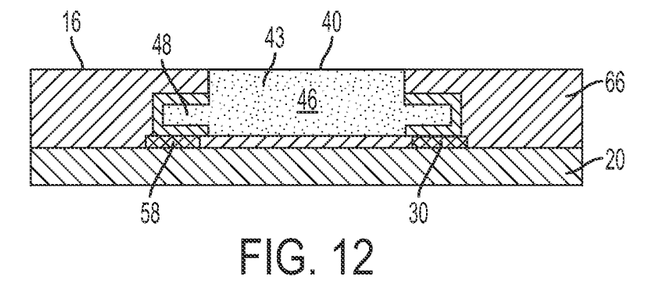
FIG. 12 illustrates a second SMD oriented within the formed cavity in the manufacture of the stretchable electronic circuit, in accordance with a representative embodiment.

Referring now to FIGS. 11 and 12, the stretchable circuit 10 can be removed from the mold container and the SMD mold removed to expose a conforming sensor cavity 62 formed into the stretchable sensor layer 66. The conforming sensor cavity 62 can include sensor contact points 58 at the locations on the exposed stretchable conductors 30 that were covered by the SMD mold's conductor contact protrusions. Furthermore, by virtue of the weight or pre-load applied to the SMD mold during manufacture, the sides of the sensor cavity 62 can also be displaced slightly in the direction of the base substrate 20.

The method further includes the step of installing a second SMD package 40 into the SMD cavity 62, with the conductor contact protrusions 48 of the second SMD package 40 contacting and establishing electrical communication with the stretchable conductors 30 on the base substrate 20 to complete a stretchable electronic circuit. In one aspect a substantially constant electrical connection can be established between the conductor contact protrusion 48 and the stretchable conductor 30 at the sensor contact points 58 by tensile forces interacting between the stretchable base substrate 20 and the stretchable sensor layer 66. The tensile forces can result from the body 46 of the second SMD package being slightly larger than the SMD cavity, which stretch the two layers apart and creates a tensile loading which can push together the conductor contact protrusions 48 and the stretchable conductors 30 at the sensor contact points 58. Additionally, the outer face 43 of the second SMD package 40 can be substantially flush with the outer surface 16 of the stretchable sensor layer 66, which can also be the outer or working surface of the stretchable electronic circuit 10.

Figure 13A:
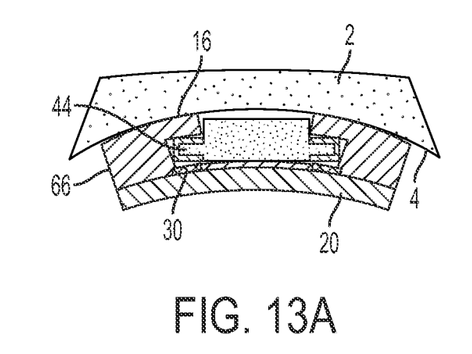
FIGS. 13A-13B together illustrate stretchability of the stretchable electronic circuit, in accordance with a representative embodiment.
Figure 13B:
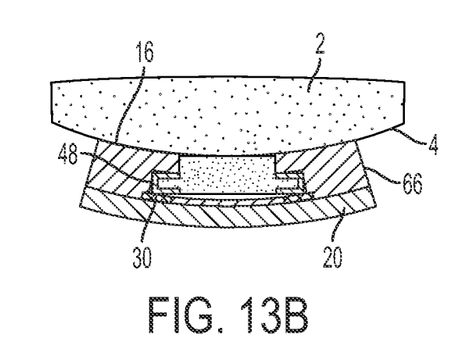

As can be seen in FIGS. 13A-13B, the electrical connection between the conductor contact protrusions 48 and the stretchable conductors 30 at the sensor contact points 58 can be affected by the surface 4 of a body member 2 against which the outer working face 16 of the stretchable electronic circuit 10 is applied. For instance, if the body surface 4 has a concave shape that forces the outer surface 16 of the stretchable electronic circuit 10 to assume a convex profile, as shown in FIG. 13A, the stretchable base substrate 20 and sensor layers 66 can tend to pull the conductors 30 away from the conductor contact protrusions 48 of the SMD package 40, which could potentially limit or break the electrical connection. Conversely, if the body surface 4 has a convex shape that forces the outer working surface 16 of the stretchable electronic circuit 10 to assume a concave profile, as shown in FIG. 13B, the stretchable base substrate 20 and sensor layers 66 can tend to push the conductors 30 further against the conductor contact protrusions 48 and strengthen the quality of the electrical connection.

FIGS. 14A-14E together illustrate additional steps in the manufacture of the stretchable electronic circuit of FIGS. 1-2 which include forming a liquid flexible electrical contact 70. In one aspect the liquid flexible electrical contact 70 can provide an external interface for the stretchable electronic circuit by creating a flexible electrical connection between an external lead wire 90 and a stretchable conductor 30.

Figure 14A:
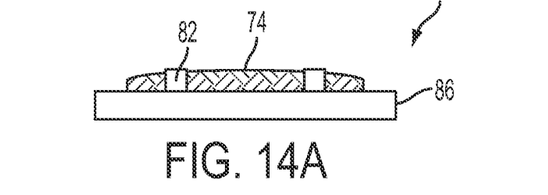
FIGS. 14A-14E together illustrate formation of liquid contact wells in the manufacture of the stretchable electronic circuit, in accordance with a representative embodiment.
Figure 14B:
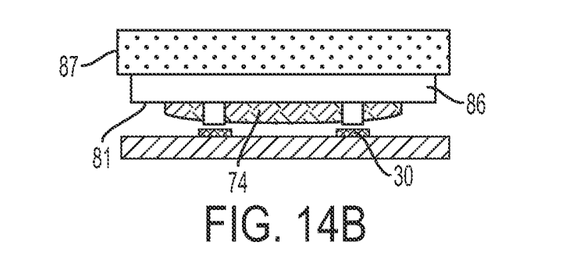

Similar to the process described above for embedding an SMD package into the stretchable electronic circuit, FIG. 14A illustrates forming an external interface mold 80 by mounting one or more protruding structures 82, such as solid, cylindrical-shaped bodies, to a second rigid plate 86. In one aspect a quantity of viscous, uncured stretchable fill material 74 can be placed on the surface of the rigid plate 86 and around the protruding structures, followed by inverting and positioning the external interface mold 80 onto the stretchable base substrate 20 with the protruding structure(s) contacting the stretchable conductor(s) 30 on the base substrate, as shown in FIG. 14B. In another aspect the external interface mold 80 can be first positioned onto the stretchable base substrate 20, followed by filling the volume 81 between the base substrate 20 and the second rigid plate 87 with uncured stretchable fill material 74. In either case a weight 87 can be placed on the backside of the rigid plate 86 to force the external interface mold 80 into the base substrate 20 and to remove any voids or pockets of air which may be trapped between the rigid plate and the base substrate. As with the stretchable sensor layer described above, the uncured stretchable fill material 74 can then be cured in various ways to form the solid stretchable connector layer 76.

Figure 14C:
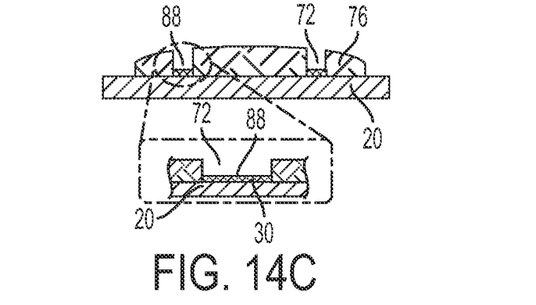

Referring now to FIG. 14C, the external interface mold 80 can be removed to expose one or more connector wells 72 formed into the stretchable connector layer 76, with each connector well 72 having a connector contact point 88 at the bottom thereof where the exposed stretchable conductor 30 was covered by the protruding structure 82.

Figure 14D:
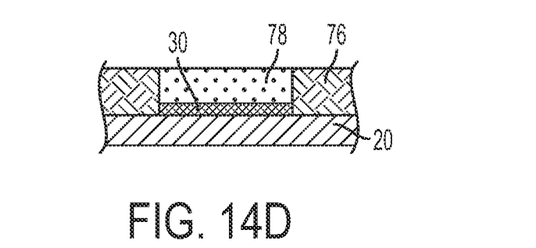
Figure 14E:
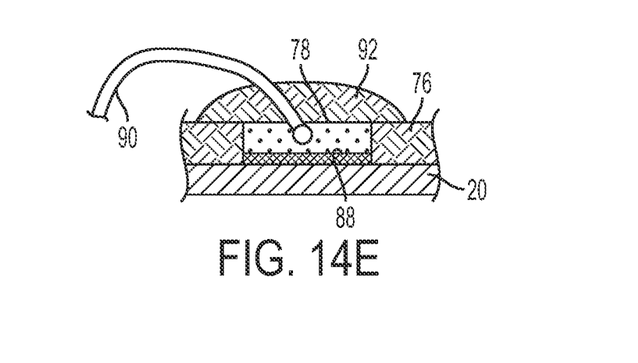

As shown in the close-up detail of FIG. 14D, upon removal of the external interface mold 80 the connector wells 72 can be filled with a non-hazardous and bio-compatible liquid metal material 78, such as EGaIn, GaInSn (Galinstan®: 68.5% Ga, 21.5% In, 10% Sn), Indalloy 60® (Indium Corp., 75.5% Ga and 24.5% In), and the like. In one aspect, the liquid metal material is EGaIn. With reference to FIG. 14E, one end of an external interface lead wire 90 can also be installed into the connector well 82 and placed into contact with the liquid metal 78 to establish a substantially constant electrical connection between the lead wire 90 and the exposed stretchable conductor 30 at the bottom of the connector well 72.

The method can further include covering the connector well 72 with a flexible or stretchable cap 92 to secure the lead wire 90 to the stretchable electronic circuit 10 and seal the liquid metal 78 within the connector well. In one aspect the connector well 72 can be covered with an uncured stretchable cap material which flows around the lead wire to form a tight seal, and which can then be cured to form the solid stretchable cap 92. However, it is contemplated that other methods and materials can also be used to secure the lead wire 90 to the stretchable circuit and seal the liquid metal 78 within the liquid well 72, and can be considered to fall within the scope of the present invention.

Figure 15A:
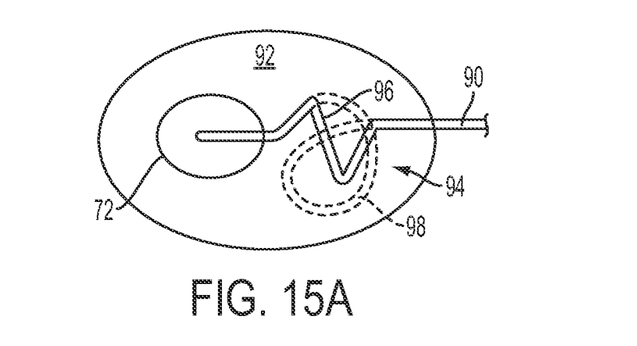
FIGS. 15A-15B are top and side schematic views, respectively, which together illustrate the lead wire anchor within liquid wells of the stretchable electronic circuit of FIG. 1.
Figure 15B:
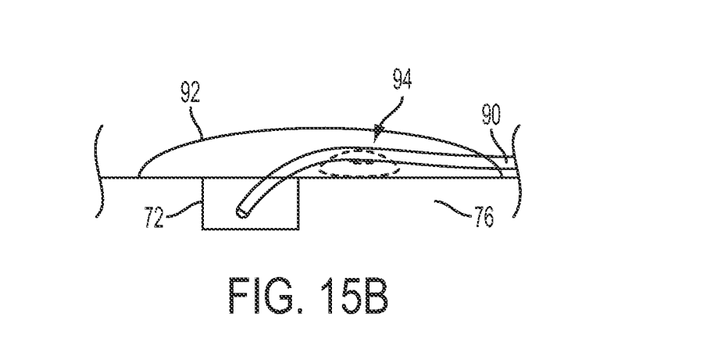

In another embodiment of the stretchable electronic circuit 10 shown in FIGS. 15A-15B, the lead wire 90 can be provided with an additional anchoring configuration 94 which can operate to better hold the wire 90 to the solid stretchable connector layer 76 and inhibit the withdrawal of the external interface lead wire from connector well 72. In one aspect the lead wire 90 can be provided with a curvature or bend 96 that increase the traction between the lead wire and the flexible or stretchable cap 92, which is in turn coupled or bonded to the stretchable connector layer 76. Alternatively, the bend 96 can also be replaced with a loop 98 or similar configuration. In yet another aspect (not shown), the tip of the lead wire 90 can also be bent, curved, flattened or otherwise modified to create an anchor point that makes contact with the inside walls the connector well 72.

Figure 16:
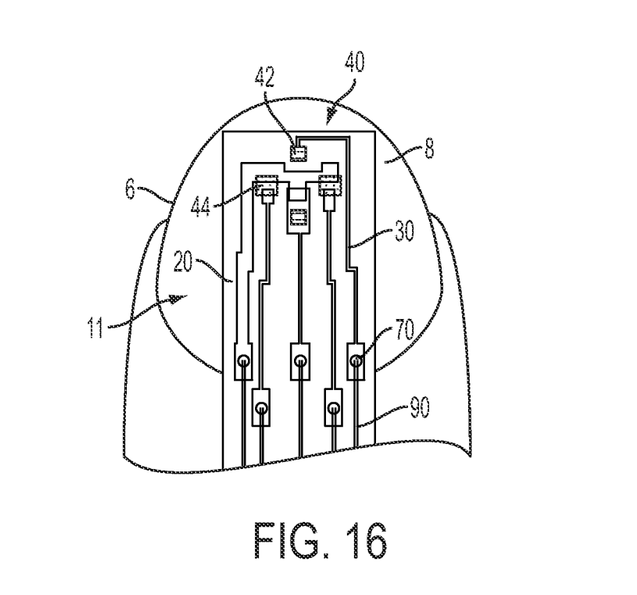
FIG. 16 is a schematic view of a finger nail sensor using an stretchable electronic circuit, in accordance with another representative embodiment.

One representative application of the stretchable electronic circuit is shown in FIG. 16, and comprises a stretchable fingernail sensor 11 for the measurement of fingertip force. The stretchable fingernail sensor 11 can be applied to the curved surface 8 of a subject's fingernail 6, with a plurality of SMD packages 40 being centered about a middle portion of the fingertip's surface 8. In this embodiment the SMD packages 40 can include two LED's 42 and two photodiode detectors 44 grouped together, and which can employ photoplethysmorgraphy to measure changes in blood perfusion in the fingernail bed when the finger touches a surface with various forces. Both optoelectronic SMD packages are embedded in a rubber-like and stretchable substrate 20 and connected to liquid flexible contacts 70 with stretchable conductors 30. Power input, signal output and common connections for each SMD package are supplied by the various external interface lead wires 90 that couple directly into the liquid flexible contacts 70. Details regarding the signal processing of collected data and associated systems can be found in U.S. Patent Application Publication 2008/0091121 and 2001/0025917 which are each incorporated herein by reference.

It is to be further appreciated that other applications also exist for the stretchable electronic circuit described herein and include, but are not limited to, pulse-oximetry for the monitoring of the oxygenation of a patient's hemoglobin, and photodynamic therapy for the activation of light-sensitive drugs applied to the skin as a cream.

The foregoing detailed description describes the invention with reference to specific representative embodiments. However, it will be appreciated that various modifications and changes can be made without departing from the scope of the present invention as set forth in the appended claims. The detailed description and accompanying drawings are to be regarded as illustrative, rather than restrictive, and any such modifications or changes are intended to fall within the scope of the present invention as described and set forth herein.

More specifically, while illustrative representative embodiments of the invention have been described herein, the present invention is not limited to these embodiments, but includes any and all embodiments having modifications, omissions, combinations (e.g., of aspects across various embodiments), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, any steps recited in any method or process claims, furthermore, may be executed in any order and are not limited to the order presented in the claims. The term "preferably" is also non-exclusive where it is intended to mean "preferably, but not limited to." Accordingly, the scope of the invention should be determined solely by the appended claims and their legal equivalents, rather than by the descriptions and examples given above.

What is claimed and desired to be secured by Letters Patent is:

1. A stretchable electronic circuit, comprising:
   a stretchable base substrate having a plurality of stretchable conductors formed onto a surface thereof; both the base substrate and conductors being bendable together about at least two orthogonal axes;
   a stretchable sensor layer attached to the base substrate and having a surface mount device (SMD) cavity formed therein, the SMD cavity including at least one contact point exposing at least one of the plurality of stretchable conductors; and
   an SMD package having a conductor contact protrusion installed into the SMD cavity, wherein tensile forces interacting between the stretchable base substrate and the stretchable sensor layer maintain a substantially constant electrical connection between the conductor contact protrusion and the stretchable conductor at the contact point.

2. The electronic circuit of claim 1, wherein the stretchable base substrate and stretchable sensor layer further comprise a biocompatible material.

3. The electronic circuit of claim 2, wherein the biocompatible material is a stretchable PDMS material.

4. The electronic circuit of claim 1, wherein the SMD package is selected from a group consisting of a light-emitting diode (LED) and a photodiode detector.

5. The electronic circuit of claim 1, further comprising:
   a stretchable connector layer attached to the base substrate and having a connector well formed therein and adjacent to at least one of the plurality of stretchable conductors;
   an external interface lead wire having one end installed with the connector well;
   flowable conductive material filling the connector well and establishing a substantially constant electrical connection between the lead wire and the stretchable conductor; and
   a stretchable cap layer over the connector well securing the lead wire to the stretchable electronic circuit and sealing the flowable conductive material within the connector well.

6. The electronic circuit of claim 5, wherein the lead wire includes an anchor to inhibit removal from the connector well.

7. The electronic circuit of claim 5, wherein the flowable conductive material is a liquid metal.

8. The electronic circuit of claim 7, wherein the liquid metal is at least one of EGaIn, GaInSn and Indalloy 60®.

9. The electronic circuit of claim 5, wherein the flowable conductive material is a conductive polymer.

10. The electronic circuit of claim 5, wherein the SMD package further comprises a plurality of light-emitting diodes and photodiode detectors arrayed together, each diode and detector being connected through a connector well to an external interface lead wire and form a sensor system attachable to a curved surface of a human body.

11. The electronic circuit of claim 10, wherein the sensor system is configured to monitor a function of the human body selected from the group consisting of fingernail blood flow and perfusion, pulse-oximetry, photodynamic therapy and combinations thereof.

12. The electronic circuit of claim 1, wherein the plurality of stretchable conductors have a buckled non-strained configuration and a stretched configuration.

13. The electronic circuit of claim 1, wherein the sensor system is configured to monitor fingernail blood flow and perfusion using photoplethysmorgraphy.

* * * * *